United States Patent [19]

Yu et al.

[11] Patent Number: 5,196,427
[45] Date of Patent: * Mar. 23, 1993

[54] 3-ARYL-4(3H) QUINAZOLINONE CCK ANTAGONISTS AND PHARMACEUTICAL FORMULATIONS THEREOF

[75] Inventors: Melvin J. Yu; Jefferson R. McCowan, both of Indianapolis; K. Jeff Thrasher, Beech Grove, all of Ind.

[73] Assignee: Eli Lilly and Company, Indianapolis, Ind.

[*] Notice: The portion of the term of this patent subsequent to Dec. 24, 2008 has been disclaimed.

[21] Appl. No.: 763,104

[22] Filed: Sep. 20, 1991

Related U.S. Application Data

[62] Division of Ser. No. 581,943, Sep. 13, 1990, Pat. No. 5,075,313.

[51] Int. Cl.$^5$ .................. A61K 31/505; C07D 403/06
[52] U.S. Cl. ..................................... 514/259; 544/284; 544/287
[58] Field of Search ................ 544/284, 287; 514/259

[56] References Cited

PUBLICATIONS

Varma et al., *Indian J. Chem.* 18B, 275–277 (1979).
Agarwal et al., *Acta Pharm. Jugosl.* 32, 37–44 (1982).
Agarwal et al., *J. Chem. Soc. Pak.* 6, 89–94 (1984).
Gupta et al., *Indian J. Chem.* 26B, 1197–1199 (1987).
Boltze, et al., *Chem. Abstr.* 63: 4289 d (1965), abstracting *Arzneim. Forsch.* 13, 688–701 (1963).

*Primary Examiner*—Mukund J. Shah
*Assistant Examiner*—Y. N. Gupta
*Attorney, Agent, or Firm*—Nancy J. Harrison; Leroy Whitaker

[57] ABSTRACT

Novel substituted quinazolinones have been found to exhibit specific binding to cholecystokinin (CCK) receptors in the brain and/or peripheral site such as the pancreas and ileum. The quinazolinones are CCK receptor antagonists and find therapeutic application in the treatment of gastrointestinal disorders and central nervous system disorders, and are useful for appetite regulation in mammals. Pharmaceutical formulations for such indications are described.

21 Claims, No Drawings

3-ARYL-4(3H) QUINAZOLINONE CCK ANTAGONISTS AND PHARMACEUTICAL FORMULATIONS THEREOF

This application is a division of application Ser. No. 07/581,943, filed Sep. 13, 1990, now U.S. Pat. No. 5,075,313.

BACKGROUND AND SUMMARY OF THE INVENTION

This invention relates to biologically active quinazolinones. More particularly, this invention is directed to certain substituted quinazolinones which bind to receptors for cholecystokinin (CCK), e.g., those of the brain and pancreas, and to receptors for gastrin, e.g., those of the stomach. The compounds are CCK and gastrin antagonists and are useful in the treatment and prevention of CCK and gastrin-related disorders of the gastrointestinal, central nervous and appetite regulatory systems of warm-blooded vertebrates, especially humans.

BACKGROUND OF THE INVENTION

Cholecystokinin (CCK) is a neuropeptide found in both gastrointestinal tissue and the tissues of the central nervous system. CCK is believed to play an important role in appetite regulation. Among the effects of CCK are stimulation of colonic motility, stimulation of gall bladder contraction, stimulation of pancreatic enzyme secretion, and inhibition of gastric emptying. CCK reportedly coexists with dopamine in certain mid-brain neurons and thus may also play a role in the functioning of dopaminergic systems in the brain. Gastrin is a neuropeptide found particularly in the gastrointestinal tract. It is one of the primary natural stimulators of gastric acid secretion. It also has growth stimulatory effects on a variety of gastrointestinal tissues.

CCK and gastrin antagonists are useful in the treatment and prevention of CCK and gastrin-related disorders of the gastrointestinal and central nervous systems, as well as modulation of the appetite regulatory systems of warm-blooded vertebrates. The CCK/gastrin receptor family is thought to contain three receptor subtypes, for which the location of the prototype receptor is given in parentheses: CCK-A (pancreas), CCK-B (brain), and gastrin (stomach fundus).

Several classes of CCK receptor antagonists have been reported in the literature. One class comprises derivatives of cyclic nucleotides, for example, dibutyryl cyclic GMP. Another art recognized class of CCK antagonists comprise the C-terminal fragments and analogs of CCK. Another class of CCK receptor antagonists are amino acid derivatives including proglumide, a derivative of glutaramic acid, and the N-acyltryptophanes such as p-chlorobenzoyl-L-tryptophan. More recently certain substituted amino phenyl compounds were described as CCK antagonists in published European Patent Application 0166355. Because of the wide range of potential clinical applications of CCK binding compounds, intensive research efforts have been ongoing to define other compounds exhibiting CCK receptor binding properties.

SUMMARY OF THE INVENTION

This invention is directed to novel quinazolinones of Formula I below which have been found to exhibit CCK and gastrin antagonist activity. These compounds are useful in the treatment and prevention of CCK-related disorders of the gastrointestinal, central nervous, and appetite regulatory systems of mammals, especially humans. As gastrin antagonists, they are particularly useful in the treatment and prevention of gastrointestinal ulcers.

DETAILED DESCRIPTION OF THE INVENTION

This invention is directed to compounds of the formula

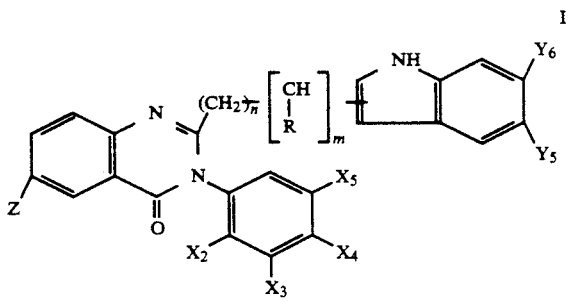

in which n is 1 or 2 and m is 0 or 1;

R is hydrogen, $C_1-C_4$ alkyl, benzyl, or phenyl;

Z is hydrogen or halo;

$X_2$, $X_3$, $X_4$, and $X_5$ are independently selected from the group consisting of hydrogen, halo, trifluoromethyl, $C_1-C_6$ alkoxy, $C_1-C_6$ alkyl, $C_1-C_6$ alkylthio, and $-NR_2R_3$, in which $R_2$ and $R_3$ are independently hydrogen, $C_1-C_4$ alkyl, benzyl, or phenyl, or $R_2$ and $R_3$ taken together with the nitrogen atom to which they are bonded form a 5- or 6-membered ring; or $X_r$ and $X_{r+1}$, in which r is 2, 3, or 4, taken together form a divalent $C_3-C_5$ alkylene group or methylenedioxy; and $Y_5$ and $Y_6$ are independently selected from the group consisting of hydrogen, $C_1-C_6$ alkyl, $C_1-C_6$ alkoxy, halo, and trifluoromethyl; and pharmaceutically acceptable salts thereof.

In the above formula, the term "$C_1-C_4$ alkyl" means a straight or branched alkyl chain having from one to four carbon atoms. Such $C_1-C_4$ alkyl groups are methyl, ethyl, n-propyl, isopropyl, n-butyl, isobutyl, sec-butyl, and t-butyl.

The term "$C_1-C_6$ alkyl" means a straight or branched alkyl chain having from one to six carbon atoms or cycloalkyl having from three to six carbon atoms. Groups which are included in such term are methyl, ethyl, n-propyl, isopropyl, cyclopropyl, n-butyl, isobutyl, methylcyclopropyl, cyclobutyl, sec-butyl, t-butyl, n-pentyl, cyclopentyl, 2-methylbutyl, 3-methylbutyl, n-hexyl, cyclohexyl, 4-methylpentyl, and the like.

The term "$C_1-C_6$ alkoxy" means a straight or branched chain alkyl group having from one to six carbon atoms or cycloalkyl having from three to six carbon atoms and joined through an oxygen atom. Groups which are included in such term are methoxy, ethoxy, n-propoxy, isopropoxy, cyclopropoxy, n-butoxy, isobutoxy, t-butoxy, sec-butoxy, cyclobutoxy, n-pentoxy, cyclopentoxy, 3-methylbutoxy, n-hexyloxy, 2-methylpentoxy, cyclohexyloxy, and the like. The term "$C_1-C_6$ alkylthio" means a straight or branched chain alkyl group having from one to six carbon atoms or cycloalkyl having from three to six carbon atoms and joined through a sulfur atom. Groups which are included in such term are methylthio, ethylthio, n-propylthio, isopropylthio, cyclopropylthio, n-butylthio, isobutylthio, t-butylthio, sec-butylthio, cyclobutylthio, n-pentylthio, cyclopentylthio, 2-methylbutylthio, n-hexylthio, 4-methylpentylthio, cyclohexylthio, and the like.

The term "halo" means any of fluoro, chloro, or bromo.

The term "$C_3$-$C_5$ alkylene" means any of —$CH_2CH_2CH_2$—, —$CH_2CH_2CH_2CH_2$—, and —$CH_2CH_2CH_2CH_2CH_2$—.

One preferred group of compounds of Formula I are those in which m is 0, n is 2, and Z is hydrogen. Another preferred group of the present compounds are those in which $Y_6$ is hydrogen and $Y_5$ is hydrogen, fluoro, chloro, or bromo. Of those preferred compounds, more preferred are those wherein $X_2$ and $X_5$ are hydrogen and at least one of $X_3$ and $X_4$ are hydrogen and the other is selected from the group consisting of $C_1$-$C_4$ alkoxy, $C_1$-$C_6$ alkyl or —$NR_2R_3$; most preferably, $X_4$ is hydrogen and $X_3$ is $C_1$-$C_4$ alkoxy.

With reference to Scheme 1 following, the present compounds are generally prepared by reaction of indole 1 and Meldrum's acid 2 and an aldehyde RCHO (formaldehyde, R=H) in the presence of proline [Diane S. Farlow, Michael E. Flaugh, Sharon D. Horvath, Edward R. Lavagnino, and Paul Pranc, *Organic Preparations and Procedures Int.* 13(1), 39 (1981)] to provide condensation adduct 3 which can be converted directly using Route C to quinazoline I by reaction with an o-aminobenzanilide 4 in the presence of pyridinium p-toluenesulfonate (PPTS) in refluxing pyridine. Alternatively, via Route A condensation adduct 3 can be decarboxylated in aqueous pyridine in the presence of copper powder to provide the intermediate indolylpropionic acid 5. The latter reacts with a methyl anthranilate 6 to form ester 7. Hydrolysis of ester 7 provides the corresponding carboxylic acid 8 which reacts at elevated temperature with an aniline hydrochloride via Route D or with an aniline in the presence of PPTS [Route E] to provide quinazoline I. Intermediate acid 8 can be prepared directly from adduct 3 by reaction with an anthranilic acid 9 in refluxing pypidine [Route B].

Scheme 1
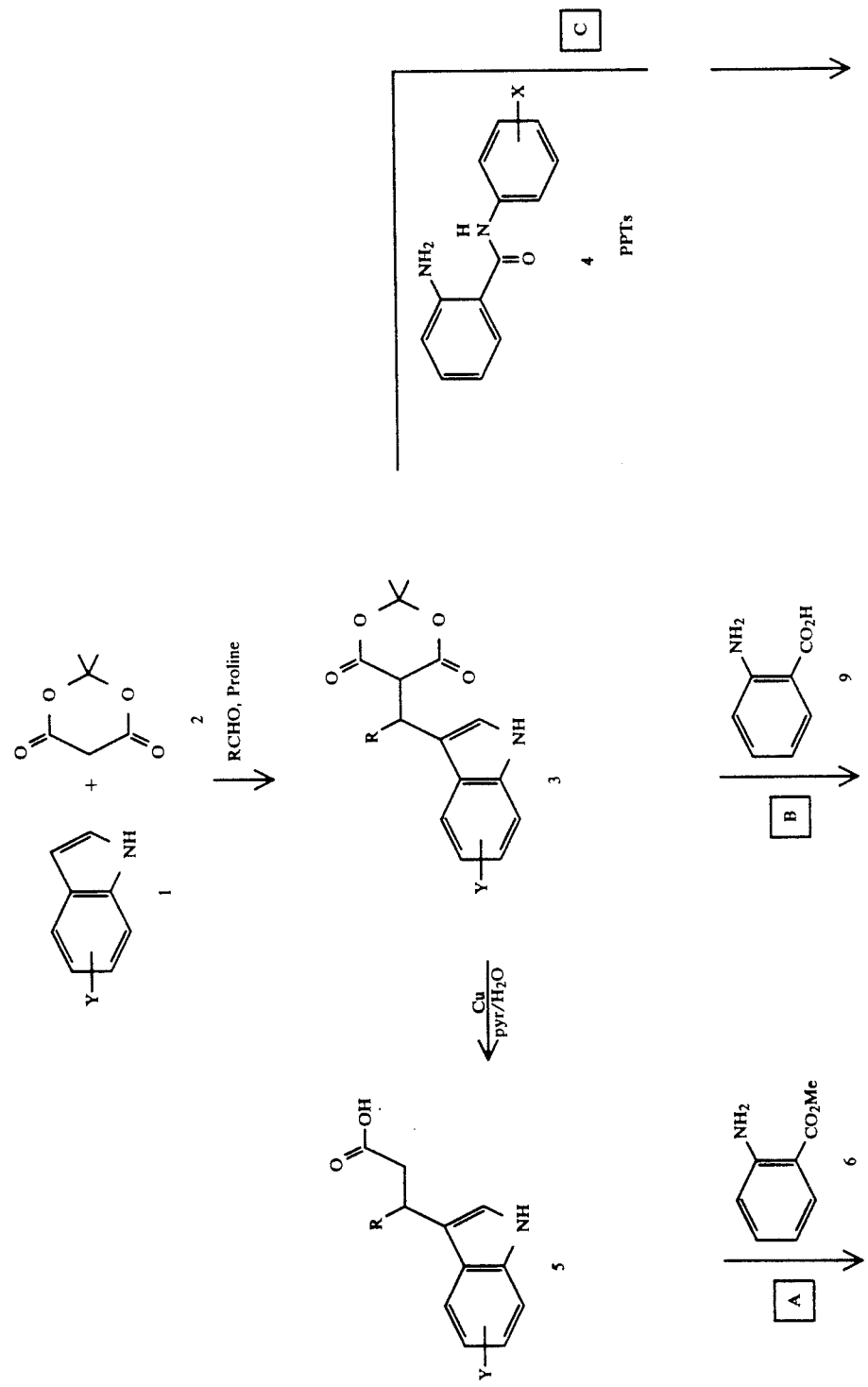

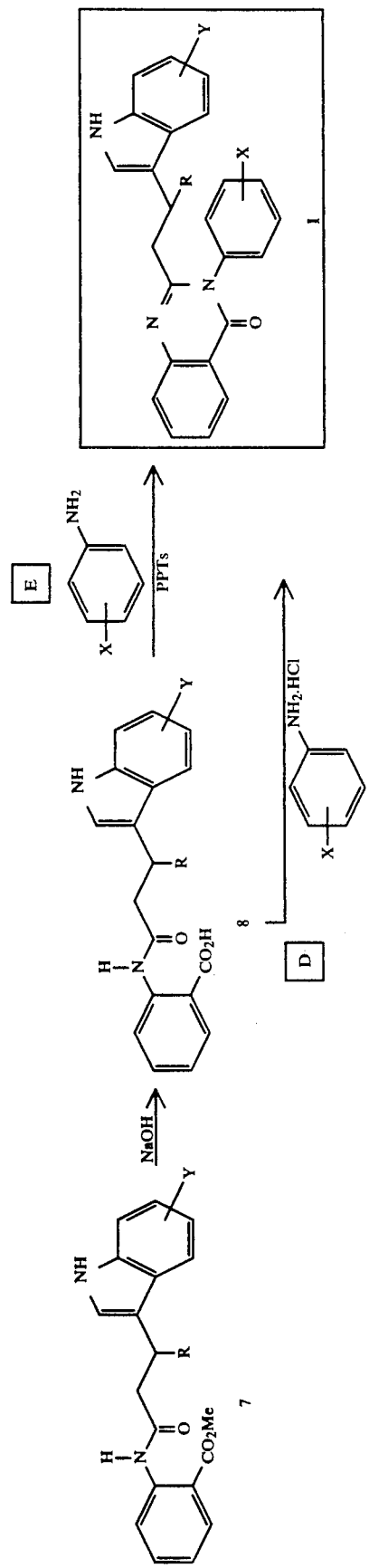

The term "pharmaceutically acceptable salts" encompasses those salts that form by standard acid-base reactions with basic groups. Thus, the pharmaceutically acceptable salts of the present invention can be prepared by conventional chemical methods from those compounds of Formula I which contain a basic moiety. Generally, the salts are prepared by reacting the free base with a stoichiometric amount or with an excess of the desired salt-forming acid in a suitable solvent or combination of solvents. Suitable salt-forming acids include inorganic acids, such as hydrochloric, hydrobromic, sulfuric, sulfamic, phosphoric, nitric, and the like; organic acids, such as acetic, propionic, succinic, glycolic, stearic, lactic, citric, malic, tartaric, ascorbic, pamoic, maleic, hydroxymaleic, phenylacetic, glutamic, benzoic, salicylic, sulfanilic, 2-acetoxybenzoic, fumaric, toluenesulfonic, methane sulfonic, ethanedisulfonic, oxalic, benzenesulfonic, picric, cinnamic, and like acids.

The compounds of this invention bind to CCK receptors in the brain and/or peripheral sites such as the pancreas, gall bladder, and ileum. Their ability to antagonize CCK and gastrin makes these compounds useful as pharmaceutical agents for the treatment and prevention of disease states wherein CCK or gastrin may be involved, for example, gastrointestinal disorders, such as irritable bowel syndrome, ulcers, excess pancreatic or gastric secretion, acute pancreatitis, motility disorders, central nervous system disorders caused by CCK's interaction with dopamine, such as neuroleptic disorders, tardive dyskinesia, Parkinson's disease, psychosis or Gilles de la Tourette Syndrome, and disorders of appetite regulatory systems.

In another embodiment of this invention there is provided pharmaceutical formulations comprising as an active ingredient an effective amount of a compound of Formula I and a pharmaceutically acceptable carrier, excipient, or diluent therefor. Such formulations can be prepared for oral or parenteral administration for the treatment and prevention of disorders of the gastrointestinal, central nervous, and appetite regulatory systems of warm-blooded vertebrates, especially man.

For oral use of an antagonist of CCK or gastrin of this invention, the selected compound can be administered, for example, in the form of tablets or capsules, or as an aqueous solution or suspension. In the case of tablets, common excipients include binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example, corn starch, gelatin, lactose, sucrose, microcrystalline cellulose, kaolin, mannitol, dicalcium phosphate, sodium chloride and alginic acid; lubricants such as magnesium stearate; disintegrants such as croscarmellose, microcrystalline cellulose, corn starch, sodium starch glycolate and alginic acid; and suitable wetting agents such as lauryl sulfate. For oral administration in capsule form, useful diluents included lactose and dried corn starch. When aqueous suspensions are desirable for oral use, the active ingredient can be combined with emulsifying and suspending agents, for example, sorbitol, methylcellulose, glucose/sugar syrup, gelatin, hydroxyethylcellulose, carboxymethylcellulose, aluminum stearate gel, or hydrogenated edible oils, for example, almond oil, fractionated coconut oil, oily esters, propylene glycol, or ethyl alcohol; flavoring agents such as pepperment, oil of wintergreen, cherry flavoring, and the like; and preservatives, such as methyl or propyl p-hydroxybenzoates and ascorbic acid.

The pharmaceutical formulations in accordance with this invention can also be prepared for parenteral use. Such formulations typically take the form of sterile isotonic solutions of the active ingredient according to standard pharmaceutical practice.

The appropriate dose of the compound of the present invention for its use as an antagonist of CCK or gastrin in humans will vary according to the age, weight and response of the individual patient, as well as the severity of the patient symptoms and the nature of the condition being treated. Thus, the preferred daily dose will normally be determined by the prescribing physician. However, in most instances, effective daily doses of the compounds of this invention will range from about 0.05 mg/kg to about 50 mg/kg and preferably from about 0.5 mg/kg to about 20 mg/kg in a single or in divided doses.

The following examples are provided to further illustrate the compounds of this invention and the methods for their preparation.

EXAMPLE 1

2-[2-(3-Indolyl)ethyl-3-phenyl-4-(3H)quinazolinone
[Route A/E]

To a solution of 3-(3-indolyl)propionic acid (6.0 g, 32 mmol) in 100 ml THF at room temperature was added 1,1-carbonyldiimidazole (5.14 g, 32 mmol). The reaction mixture was stirred under a dry atmosphere for 30 minutes, after which methyl anthranilate (4.79 g, 32 mmol) was added, and the reaction mixture was stirred at reflux for 30 minutes. No reaction was detected by thin layer chromatography (TLC). Pyridinium p-toluenesulfonate (PPTS) [6.36 g, 25 mmol] was added, and the mixture was stirred at reflux for two days. The reaction mixture was allowed to cool, and the solvent was removed in vacuo. The resulting product was taken up in ethyl acetate and washed (1N HCl, $H_2O$, saturated $NaHCO_3$, and brine) and dried over anhydrous magnesium sulfate. Concentration in vacuo provided a light yellow solid which, when triturated with ethyl acetate/hexane, gave, upon filtration, 7.19 g (70% yield) of 3-(3-indolyl)-N-(2-methoxycarbonylphenyl)propionamide as an off white granular solid.

The methyl ester product (7.19 g, 22.3 mmol) was dissolved in 75 ml methanol and 25 ml 1N sodium hydroxide. The reaction mixture was stirred at reflux for 30 minutes, cooled to room temperature, and concentrated in vacuo. The aqueous residue was diluted with water and washed once with diethyl ether. The aqueous phase was separated, acidified with 40 ml of 1N HCl, and extracted with ethyl acetate. The organic layer was washed with brine and dried over anhydrous sulfate. Evaporation to dryness in vacuo provided a solid which, upon trituration with 40% ethyl acetate/hexanes and filtration, provided 6.34 g (92% yield) of an off-white, granular solid, the physical chemical data for which [MS 308 (M+)] was consistent with that expected for the intermediate 3-(3-indolyl)-N-(2-carboxyphenyl)propionamide.

To a solution of 3-(3-indolyl)-N-(2-carboxyphenyl)-propionamide (6.20 g, 20 mmol) in 50 ml of THF at room temperature was added 1,1-carbonyldiimidazole (3.26 g, 20 mmol). The reaction mixture was stirred under a dry atmosphere for 30 minutes after which aniline (2 ml, 22 mmol) and PPTS (4.03 g, 16 mmol)

were added. The resulting reaction mixture was stirred under reflux for two days. The reaction mixture was allowed to cool and evaporated to dryness in vacuo. The product residue was taken up in ethyl acetate and washed (1N HCl, water, saturated NaHCO$_3$, and brine), dried over anhydrous sodium sulfate, and concentrated in vacuo to a brown oil which crystallized from ethyl acetate/hexanes. The product was recrystallized from methanol/ethyl acetate to provide 2.28 g of 2-[2-(3-indolyl)ethyl]-3-phenyl-4-(3H)quinazolinone as white fluffy needles; m.p. 193°-194° C.; FABMS and EIMS 366 (M+); IR (KBr) 1672 CM$^{-1}$.

Analysis, calculated for C$_{24}$H$_{19}$N$_3$O:
Calc.: C, 78.88; H, 5.24; N, 11.50;
Found: C, 78.65; H, 5.26; N, 11.36.

EXAMPLE 2

2-(3-Indolylmethyl)-3-phenyl-4-(3H)quinazolinone

[Route A/E modified To a solution of 3-indoleacetic acid (5.79 g, 33.1 mmol) in 100 ml THF at room temperature was added 1,1-carbonyldiimidazole (5.36 g, 33.1 mmol). The reaction mixture was stirred for 15 minutes under nitrogen. Methyl anthranilate (5.0 g, 33.1 mmol) and PPTS (20.0 g, 80 mmol) were added to the reaction mixture which was then stirred at reflux for 24 hours, cooled, and concentrated to near dryness in vacuo. The product residue was partitioned between 1N hydrochloric acid and ethyl acetate. The two-phase mixture was heated until two clear layers were obtained. The aqueous layer was separated and the organic layer was allowed to cool, washed (water, 1N NaOH, and brine), dried over anhydrous sodium sulfate, and concentrated in vacuo to dryness. The resulting product was triturated with ethyl acetate/hexane and collected by vacuum-assisted filtration to give 8.85 g of 2-(3-indolyl)-N-(2-methoxycarbonylphenyl)acetamide as a pale yellow granular solid which was deesterified by refluxing it in a mixture of 100 ml of methanol and 32 ml of 1M NaOH for 30 minutes. The product acid was isolated by concentrating the deesterification mixture in vacuo, acidifying with 40 ml of 1N hydrochloric acid, and then extracting it into ethyl acetate. The organic layer was washed with brine, dried over anhydrous sodium sulfate, and concentrated in vacuo to dryness. Trituration with ethyl acetate/hexanes and vacuum-assisted filtration provided 8.0 g of 2-(3-indolyl)-N-( 2-carboxyphenyl)acetamide as an off-white solid: mp 205°-207° C.

Analysis, calculated for C$_{17}$H$_{14}$N$_2$O$_3$:
Calc.: C, 69.38; H, 4.79; N, 9.52;
Found: C, 69.29; H, 4.93; N, 9.45.

To a solution of the above product (7.0 g, 23.8 mmol) in 100 ml THF at room temperature was added 1,1-carbonyldiimidazole (4.24 g, 26.2 mmol). The reaction mixture was stirred for 30 minutes after which aniline (2.4 ml, 26 mmol) and PPTS (15.8 g, 63 mmol) were added. The reaction mixture was stirred at reflux for 2 days under nitrogen, cooled, and concentrated to near dryness in vacuo. The residue was partitioned between ethyl acetate and 1N hydrochloric acid. The organic phase (which contained an undissolved solid) was washed once with 1N hydrochloric acid and 3 times with water. The organic phase was separated and evaporated in vacuo. The residue was taken up in toluene and again concentrated to near dryness. The resulting solid was triturated with ethyl acetate/hexanes and collected by vacuum-assisted filtration. The product was then dispersed in methanol/ethyl acetate, heated to boiling, and allowed to cool. Vacuum-assisted filtration provided 3.08 g of 2-(3-indolyl)-N-(2-anilinocarbonylphenyl)acetamide as white needles: mp 235°-236.5° C.; FDMS: 369 (M+).

Analysis, calculated for C$_{23}$H$_{19}$N$_3$O$_2$:
Calc.: C, 74.78; H, 5.18; N, 11.37;
Found: C, 75.15; H, 5.10; N, 11.33.

A mixture of 500 mg of the above product, and 26 mg of p-toluenesulfonic acid in 20 ml of toluene was refluxed under drying tube with azeotropic removal of water for 3 hours. Additional p-toluenesulfonic acid (26 mg) was added to the reaction mixture before it was refluxed for an additional 21 hours. The mixture was cooled, diluted with ethyl acetate, washed (saturated NaCO$_3$ and brine), dried over anhydrous sodium sulfate, and concentrated in vacuo to near dryness. The residue was triturated with methanol/ethyl acetate and filtered. The filtrate was concentrated in vacuo and chromatographed (50% ethyl acetate/hexanes, SiO$_2$) to give the titled product as a yellow oil which crystallized from ethyl acetate/hexanes as fine white needles (150 mg): mp 191°-192° C.; EIMS: 351 (M+).

Analysis, calculated for C$_{23}$H$_{17}$N$_3$O:
Calc.: C, 78.61; H, 4.88; N, 11.96;
Found: C, 78.79; H, 4.96; N, 12.02.

EXAMPLE 3

2-[2-(5-Methoxyindol-2-yl)ethyl]-3-phenyl-4-(3H)quinazolinone [Route A/D]

A solution of 5-methoxyindole (10.0 g, 67.9 mmol), 5.5 ml formaldehyde (37% aqueous solution), Meldrum's acid (10 g, 69 mmol), and proline (0.4 g) in 40 ml of acetonitrile was stirred at room temperature for 16 hours. The reaction mixture was concentrated in vacuo to provide a brown foam. The product was taken up in about 50 ml of acetone, and about 50 ml of water was added to the cloud point. The mixture was allowed to stand in the freezer and, after crystallization began, additional water was added with swirling again to the cloud point. Vacuum-assisted filtration provided 16.2 g of 2-(2,2-dimethyl-4,6-dioxo-1,3-dioxan-5-yl)methyl-5-methoxyindole as sand-colored crystals.

The product (16.2 g, 53.4 mmol), copper powder (390 mg), and water (15 ml) in 140 ml of pyridine was refluxed for 3 hours. The reaction mixture was cooled, filtered, and concentrated in vacuo to near dryness. The product was taken up in toluene and the resulting mixture again concentrated in vacuo to dryness. The residue was then dissolved in one liter of diethyl ether, washed (500 ml of 1N hydrochloric acid, 500 ml 20% aqueous ammonium chloride, water, and brine), dried over anhydrous sodium sulfate, and concentrated in vacuo to dryness. Crystallization of the product from chloroform/hexane yielded 9.94 g (85%) of 3-(5-methoxyindol-3-yl)propionic acid as a brown powder:mp 123°-128° C.

To a solution of of the foregoing product (6.95 g, 31.7 mmol) in 100 ml THF at room temperature under a drying tube was added 1,1-carbonyldiimidazole (5.14 g, 31.7 mmol). The reaction mixture was stirred for one hour after which methyl anthranilate (4.79 g, 31.7 mmol) and PPTS (7.96 g, 31.7 mmol) were added. The reaction mixture was stirred at reflux for three days after which an additional 7.96 g of PPTS was added, and was continued for 2 days. The reaction mixture was cooled, diluted with ethyl acetate, washed (1N hydrochloric acid, water, saturated sodium bicarbonate, and brine), dried over anhydrous sodium sulfate, and concentrated in vacuo to dryness. Crystallization of the resulting residue from ethyl acetate/hexanes provided 5.21 g (47%) of 3-(5-methoxyindol-3-yl)-N-(2-methoxycarbonylphenyl)propionamide.

The foregoing propionamide ester (5.2 g) was dissolved in a mixture of 50 ml of methanol and 16.5 ml of 1N sodium hydroxide solution, and the mixture was refluxed for 30 minutes, cooled, and concentrated in vacuo to near dryness. The product residue was diluted with water and washed once with ether. The aqueous layer was acidified with 20 ml of 1N hydrochloric acid and extracted with ethyl acetate. The organic layer was separated, washed with brine, dried over anhydrous sodium sulfate, and concentrated in vacuo to dryness. Crystallization of the product from ethyl acetate/hexane provided 4.53 g (91% yield) of 3-(5-methoxyindol-3-yl)-N-(2-carboxyphenyl)propionamide as a brown powder: mp 168°–170° C.; FDMS: 338 (M+).

Analysis, calculated for $C_{19}H_{18}N_2O_4$:
Calc.: C, 67.45; H, 5.36; N, 8.28;
Found: C, 67.26; H, 5.63; N, 8.07.

To a solution of 3-(5-methoxyindol-3-yl)-N-(2-carboxyphenyl)propionamide (4.0 g, 11.8 mmol) in 50 ml of THF at room temperature was added 1,1-carbonyldiimidazole (1.92 g, 11.8 mmol). The reaction mixture stirred for one hour after which aniline hydrochloride (3.06 g, 23.6 mmol) and 25 ml of dimethylformamide were added. The reaction mixture was stirred at reflux under a drying tube for two days, allowed to cool, and concentrated in vacuo to dryness. The residue was partitioned between 1N hydrochloric acid and ethyl acetate. The organic layer was washed (water, 1N sodium hydroxide, and brine), dried over anhydrous sodium sulfate, and concentrated in vacuo to dryness. Crystallization of the product from ethyl acetate/trace methanol provided 1.86 g of 2-[2-(5-methoxyindol-3-yl)-ethyl]-3-phenyl-4-(3H)quinazolinone as a white powder: mp 220°–221° C.; EIMS: 395 (M+).

Analysis, calculated for $C_{25}H_{21}N_3O_2$:
Calc.: C, 75.93; H, 5.35; N, 10.63;
Found: C, 75.65; H, 5.30; N, 10.35.

The foregoing intermediate product 3-(5-methoxyindol-3-yl)-N-(2-carboxyphenyl)propionamide can be prepared directly from the corresponding Meldrum's Adduct [3-(2,2-dimethyl-4,6-dioxo-1,3-dioxane-5-yl)-methyl-5-methoxyindole] (4.41 g, 14.5 mmol) by reaction with an equivalent amount of anthranilic acid (1.99 g, 14.5 mmol) in 30 ml of pyridine. The reaction is carried out at reflux for two hours after which the pyridine is azeotropically removed under vacuum with toluene [Route B].

EXAMPLE 4

2-[2-(5-Bromoindol-3-yl)ethyl]-3-(3-isopropoxyphenyl)-4-quinazolinone [Route C]

3-Nitrophenol (50.0 g, 360 mmol), isopropyl iodide (76.19 g, 450 mmol), and potassium carbonate (60 g) were combined and refluxed under nitrogen overnight in 400 ml of acetone. The reaction mixture was cooled, and the solvent was removed in vacuo. The reaction was combined with about 300 ml of water and thereafter extracted with four 100 ml portions of ethyl acetate. The ethyl acetate extracts were combined and washed twice with 1N sodium hydroxide and brine, dried over anhydrous sodium sulfate, and evaporated to provide 56 g (86%) of 3-isopropoxynitrobenzene as a clear yellow oil.

A solution of 3-isopropoxynitrobenzene (8.5 g, 50 mmol) and $PtO_2$ (0.3 g) in 200 ml of ethanol was shaken under 40 psi hydrogen at room temperature for 1.5 hours. The mixture was filtered through Celite, and the filtrate was concentrated in vacuo to provide 7.08 g of light oil (3-isopropoxyaniline). The oil was added to isatoic anhydride (7.35 g, 45 mmol) along with 15 ml of ethyl acetate. The mixture was heated in a 90° oil bath under nitrogen for two hours. The product crystallized from the reaction mixture upon the addition of hexanes. Filtration of the reaction mixture provided 10.19 g (83%) of 2-amino-N-(3-isopropoxyphenyl)benzamide as a white solid.

A solution of 5-bromoindole (10.07 g, 51 mmol), Meldrum's acid (7.38 g, 51 mmol), proline (1.24 g), and 5.2 ml of 30% aqueous formaldehyde in 100 ml of acetonitrile was allowed to stand at room temperature for 24 hours. The acetonitrile was removed in vacuo. Crystallization of the product from methanol (50 ml) provided 15.83 g of 3-(2,2-dimethyl-4,6-dioxo-1,3-dioxane-5-yl)methyl-5-bromoindole as a white solid.

A solution of 3-(2,2-dimethyl-4,6-dioxo-1,3-dioxane-5-yl)methyl-5-bromoindole (4.12 g, 12 mmol), 2-amino-N-(3-isopropoxyphenyl)benzamide (3.48 g, 13 mmol), and PPTS (1.64 g, 6.5 mmol) in 50 ml of pyridine was refluxed for 3.5 days. The reaction mixture was then evaporated in vacuo to dryness, and the residue was taken up in methylene chloride. The product was chromatographed (30% ethyl acetate/hexanes, $SiO_2$) and the title product (2.13 g, 36%) crystallized by allowing the fractions containing product to evaporate: mp 179°–181° C.

Analysis, calculated for $C_{27}H_{24}N_3O_2Br$:
Calc.: C, 64.55; H, 4.81; N, 8.36;
Found: C, 64.79; H, 5.01; N, 8.36.

EXAMPLE 5

2-[2-Phenyl-2-(3-indolyl)ethyl]-3-(3-methoxyphenyl)-4-(3H)quinazolinone [Route C modified]

Indole (10 g, 85 mmol), Meldrum's acid (12.3 g, 85 mmol), benzaldehyde (18.11 g, 171 mmol) and proline (0.05 g) were combined with 50 ml of acetonitrile and stirred in an oil bath at approximately 35°–40° C. for two hours [Y. Oikawa, H. Hirasawa, and O. Honemitsu, Tetrahedron Letters, 1759 (1978)]. The reaction mixture was concentrated in vacuo to dryness. The residue was slurried with methanol and filtered to provide 19.99 grams of 3-[α-(2,2-dimethyl-4,6-dioxo-1,3-dioxane-5-yl)benzyl]indole. A portion of the product was recrystallized from ethyl acetate to provide a white crystalline product: mp 147°–150° C.

Analysis, calculated for $C_{21}H_{19}NO_4$:
Calc.: C, 72.19; H, 5.48; N, 4.01;
Found: C, 72.19; H, 5.61; N, 4.08.

Isatoic anhydride (32.63 g, 200 mmol) and 3-methoxyaniline (24.63 g, 200 mmol) were combined neat and heated at 120° C. for 2 hours. The reaction product was taken up in methylene chloride and chromatographed (20% ethyl acetate/hexanes, $SiO_2$), to provide 38.75 g (80%) of 2-amino-N-(3-methoxyphenyl)benzamide. An analytical sample was obtained by recrystallization from ethyl acetate: mp 75°–77° C.

Analysis, calculated for $C_{14}H_{14}N_2O_2$:
Calc.: C, 69.40; H, 5.82; N, 11.56;
Found: C, 69.63; H, 5.84; N, 11.60.

2-Amino-N-(3-methoxyphenyl)benzamide (2.77 g, 11.5 mmol), 3-[α-(2,2-dimethyl-4,6-dioxo-1,3-dioxane-5- yl)benzyl]indole (4.00 g, 11.5 mmol), and PPTS (1.44 g, 5.7 mmol) in 20 ml of pyridine was refluxed for seven days. The reaction mixture was concentrated in vacuo to an oil and partitioned between ethyl acetate and water. The ethyl acetate layer was separated, washed (1N hydrochloric acid, saturated sodium bicarbonate, and brine), dried over anhydrous sodium sulfate, and concentrated in vacuo to dryness. The reaction was incomplete. The product was therefore mixed with PPTS (3 g) and 10 ml of 2,4,6-collidine and refluxed for five hours. The product was worked up as above to provide an oil which, upon standing for about one month, began to crystallize. Trituration with ethyl acetate and filtration provided 1.4 g of the title product: mp 160°–164° C.

Analysis, calculated for $C_{31}H_{25}N_3O_2 \cdot \frac{1}{4}C_4H_8O_2$:
Calc.: C, 77.53; H, 5.57; N, 8.39;
Found: C, 77.58; H, 5.45; N, 8.47.

Test Procedures for CCK And Gastrin Receptor Binding ($IC_{50}$)

Brain

Brain CCK receptor binding was performed using mouse brain membranes according to the method of Chang and Lotti (*Proc. Natl. Acad. Sci.* 83: 4923–4926, 1986). Male CF-1 mice, 23–25 g were sacrificed by cervical dislocation, the forebrain removed and placed in ice cold 50 mM Tris buffer, pH 7.4. The tissue was homogenized in 100 volumes of the Tris buffer with a Brinkman Polytron or Tekmar Tissumizer and then centrifuged at 40,000 g for 10 min. Pellets were resuspended in Tris buffer, centrifuged as above and then resuspended in 100 volumes of assay buffer, pH 6.5 (20 mM N-2-hydroxyethyl-piperazine-N'-2-ethane sulfonic acid (HEPES), 1 mM ethylene glycol bis(2-aminoethyl ether-N,N,N',N'-tetraacetic acid) (EGTA), 5 mM $MgCl_2$, 130 mM NaCl, and 0.25 mg/ml bacitracin). The binding assay consisted of 50 µL of compound (or buffer for total binding), 50 µL of $^{125}I$-CCK-8 sulfate (20 pM) (Amersham IM-159), 200 µL of assay buffer and 200 µL of homogenate (80–120 µg protein). The samples were incubated at room temperature (25°) for 2 hours, and they were then filtered through GF/B glass fiber filters (soaked in wash buffer for 2 hours before use) using a 48 well Brandel cell harvester designed for receptor binding. The filters were washed twice with 3 ml of 50 mM Tris buffer, pH 7.4, containing 0.01% BSA and then counted for radioactivity in plastic tubes with a Micromedic 10/600 automatic gamma counter.

Compounds were dissolved in dimethyl sulfoxide (DMSO) at a concentration of 10 mM and then further diluted with assay buffer. The concentration of DMSO in the incubation was 0.1% or less and had no effect on the assay at that level. IC-50 values of displacement curves were determined using 7 concentrations of compound and were calculated using the ALLFIT computer program of DeLean, Munson and Rodbard (*Am. J. Physiol.* 235: E97-E102, 1978). Non-specific binding was determined as the displacement of the radioligand by 100 nM CCK-8 sulfate.

Pancreas

Binding to peripheral type CCK receptors in rat pancreas was done according to the method of Chang et al. (*Mol. Pharmacol.* 30: 212-217, 1986) using $^3H$-L364, 718. Pancreas was obtained from male & Sprague-Dawley rats, 150–200 g, after decapitation, and dissected free from adipose and connective tissue. The tissue was homogenized in 30 volumes of 50 mM Tris buffer, pH 7.4 and centrifuged at 40,000 g for 10 min. The tissue pellet was washed by resuspension and centrifugation as described above. The final pellet was suspended in 500 volumes of assay buffer (50 mM Tris buffer, pH 7.4, 5 mM $MgC_2$, 0.14 mg/ml bacitracin, and 5 mM dithiothreitol) to give a protein concentration of 30–60 µg/200 µl. Reagent volumes for the assay were the same as those used for CCK binding to brain membranes. Tritium labeled L-364,718 (Dupont NEN, NET-971) was used as the ligand at a concentration of 0.4–0.6 nM. The samples were incubated 1 hour at room temperature and then filtered as described for the CCK-brain receptor. Scintillation cocktail was added to the filters which were counted for radioactivity using a Micromedic Taurus automatic liquid scintillation counter.

Compound samples were prepared and IC-50 values were determined as described for the CCK-brain experiments. Non-specific binding was that amount left bound to the filters after adding 100 nM L-364,718.

Gastric Mucosa

The method used for gastrin binding to guinea pig stomach mucosal membranes was similar to that described by Takeuchi, Speir and Johnson (*Am. J. Physiol.* 237(3): E284–E294, 1979). Guinea pig stomach fungus was obtained from male Hartley guinea pigs, 300–350 g, and the mucosa was scraped off with a glass The mucosa was homogenized in 50 mM Tris buffer, pH 7.4, containing 1 mM phenylmethanesulfonyl fluoride using a Dounce glass homogenizer, and the suspension was centrifuged at 40,000 g for 10 min. The resulting pellet was resuspended and centrifuged once more, the final pellet was then suspended in 100 ml assay buffer per 1 guinea pig stomach to give a protein concentration of 200–300 µg/200 µl. The assay buffer consisted of 50 mM Tris buffer, pH 7.4, 5 mM $MgC_2$, 0.14 mg/ml bacitracin, and 1 µg/ml each of leupeptin, chymostatin, aprotinin and pepstatin. Reagent volumes for the assay were the same as those used for CCK binding to brain membranes. The radioactive ligand was 20 pM $^{125}I$-gastrin I, from DuPont NEN (NEX-176). The samples were incubated 3 hours at room temperature and filtered and counted as described for CCK binding to brain membranes. Compound samples were prepared and IC-50 values were determined as described for the CCK-brain receptor binding. Non-specific binding was determined using 100 nM gastrin I (human synthetic from Sigma Chemical Co.).

Physical data, receptor binding data, and preparative methods are provided in Table I following for the foregoing Examples 1–5 as well as additional Examples 6–66. The compound of each example is identified by reference to the structural formula preceding each group of examples. The method for preparing each compound is indicated by reference to Procedure A–E corresponding to the procedures identified in the foregoing Examples 1–5 and Scheme 1.

TABLE 1

Melting Point, Preparative Method, and CCK and Gastrin Receptor Binding Data

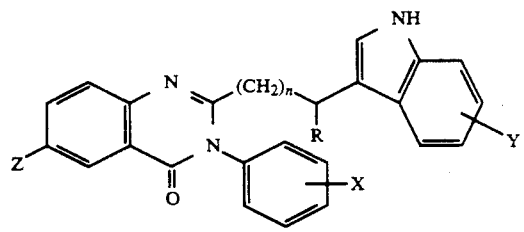

| Example | X | Y | Z | n | R | m.p. (°C.) | Procedure | Brain[1] | Pancreas[1] | Gastrin[1] |
|---|---|---|---|---|---|---|---|---|---|---|
| 1 | H | H | H | 1 | H | 193–194 | A, E | 0.67 ± 0.15[7] | 37% (10 μM) | |
| 2 | H | H | H | 0 | H | 191–192 | A, E[5] | 36% (10 μM) | | |
| 3 | H | 5-MeO | H | 1 | H | 220–221 | A, D | 0.41 | | |
| 4 | 3-iPrO | 5-Br | H | 1 | H | 179–181 | C | 0.0093 ± 0.0015[7] | −1.4% (10 μM) | 0.16 ± 0.04[7] |
| 5 | 3-MeO | H | H | 1 | Ph | 160–164 | C[6] | 57% (1 μM) | | |
| 6 | H | 5-Cl | H | 1 | H | 228–229.5 | B, D | 85%, 23% (1 μM) | | |
| 7 | H | 6-Cl | H | 1 | H | 114–117 (dec) | A, D | 1.1 | | |
| 8 | 2-F | H | H | 1 | H | 137–139 | A, E[2] | 75% (10 μM) | | |
| 9 | 2-Cl | H | H | 1 | H | 182–185 | A, E[2] | 44% (10 μM) | | |
| 10 | 2-MeO | H | H | 1 | H | 161–162 | A, E[2] | 74% (10 μM) | | |
| 11 | 2-CF$_3$ | H | H | 1 | H | 149–150 | A, E[2] | 35% (10 μM) | | |
| 12 | 3-F | H | H | 1 | H | 165.5–167.5 | C | 0.73 ± 0.17[7] | 11% (10 μM) | |
| 13 | 3-Cl | H | H | 1 | H | 164–166 | A, E[3] | 0.69 ± 0.16[7] | 17% (10 μM) | |
| 14 | 3-Me | H | H | 1 | H | 175–177 | C | 0.15 ± 0.01[7] | 0.6% (10 μM) | |
| 15 | 3-Br | H | H | 1 | H | 163–165 | C | 0.37 ± 0.03[7] | −5.7% (10 μM) | |
| 16 | 3-Br | 5-Cl | H | 1 | H | 209–211 | C | 0.19 | 2% (10 μM) | |
| 17 | 3-MeO | H | H | 1 | H | 151–152 | A, E[2] | 0.16 ± 0.03[7] | 16% (10 μM) | |
| 18 | 3-MeO | 5-F | H | 1 | H | 229–231 | C | 0.11 ± 0.01[7] | | |
| 19 | 3-MeO | 5-Cl | H | 1 | H | 234–236 | C | 0.047 ± 0.003[7] | | |
| 20 | 3-MeO | 5-Br | H | 1 | H | 219–221 | C | 0.038 ± 0.003[7] | 5.3% (10 μM) | 1.3 ± 0.4[7] |
| 21 | 3-MeO | 5-Me | H | 1 | H | 169–171 | C | 0.055 ± 0.003[7] | | |
| 22 | 3-MeO | 5-MeO | H | 1 | H | 166–168 | C | 0.067 ± 0.005[7] | | |
| 23 | 3-EtO | 5-Br | H | 1 | H | 224–226 | C | 0.034 ± 0.007[7] | −14% (10 μM) | |
| 24 | 3-EtO | 5-MeO | H | 1 | H | 204–206 | C | 0.033 | | |
| 25 | 3-iPrO | H | H | 1 | H | 158–161 | C | 0.026 ± 0.0003[7] | | |
| 26 | 3-iPrO | 5-Cl | H | 1 | H | 179–181 | C | 0.019 ± 0.005[7] | | |
| 27 | 3-iPrO | 5-MeO | H | 1 | H | 166–168 | C | 0.019 | | |
| 28 | 3-Et | H | H | 1 | H | 157–159 | B, D[4] | 0.072 ± 0.001[7] | 2.6% (10 μM) | 1.1 ± 0.2[7] |
| 29 | 3-Et | 5-Br | H | 1 | H | 166–168 | C | 0.046 ± 0.010[7] | −4.5% (10 μM) | |
| 30 | 3-Et | 5-Cl | H | 1 | H | 157–160 | C | 0.030 | −9.1% (10 μM) | |
| 31 | 3-Et | 5-MeO | H | 1 | H | 195–197 | C | 0.022 | 11% (10 μM) | |
| 32 | 3-MeS | 5-Br | H | 1 | H | 183–185 | C | 0.046 ± 0.008[7] | | |
| 33 | 3-MeS | 5-MeO | H | 1 | H | 138–140 | C | 0.034 | | |
| 34 | 3-CF$_3$ | 5-Br | H | 1 | H | 175–177 | C | 0.23 ± 0.03[7] | | |
| 35 | 3-CF$_3$ | 5-Cl | H | 1 | H | 154–158 | C | 0.23 | | |
| 36 | 3-CF$_3$ | 5-Me | H | 1 | H | 152–155 | C | 0.19 | | |
| 37 | 3-CF$_3$ | 5-MeO | H | 1 | H | 218–220 | C | 0.13 | | |
| 38 | 3-NMe$_2$ | 5-Br | H | 1 | H | 242–244 | C | 0.016 ± 0.001[7] | | |
| 39 | 3-NMe$_2$ | 5-Cl | H | 1 | H | 225–227 | C | 0.013 | | |
| 40 | 3-pyrrolidino | 5-Br | H | 1 | H | 250–251 | C | 0.022 ± 0.003[7] | | |
| 41 | 3,5-diMeO | H | H | 1 | H | 224–225 | A, E[2] | 1.8 | | |
| 42 | 3,4-OCH$_2$O | H | H | 1 | H | 189–191 | A, E[2] | 0.19 ± 0.04[7] | | |
| 43 | 4-MeO, 3-nPr | 5-Br | H | 1 | H | 221–223 | C | 85% (1 μM) | | |
| 44 | 4-EtO, 3-Me | 5-Br | H | 1 | H | 215–217 | C | 0.065 | | |
| 45 | 3-Me, 4-MeO | 5-Br | H | 1 | H | 241–243 | C | 0.029 | | |
| 46 | 3,4-diMeO | 5-Br | H | 1 | H | 226–229 | C | 0.13 ± 0.03[7] | | |
| 47 | 4-Et | 5-Br | H | 1 | H | 250–253 | C | 0.028 ± 0.004[7] | | |
| 48 | 4-iPr | 5-Br | H | 1 | H | 238–240 | C | 0.037 ± 0.013[7] | | |
| 49 | 4-iPr | 5-Cl | H | 1 | H | 240–241 | C | 0.038 | | |
| 50 | 4-nBu | 5-Br | H | 1 | H | 238–240 | C | 0.93 | | |
| 51 | 4-MeO | H | H | 1 | H | 229–230 | A, E[2] | 0.098 ± 0.007[7] | | |
| 52 | 4-MeO | 5-Br | H | 1 | H | 252–253 | C | 0.031 ± 0.006[7] | 0.3% (10 μM) | |
| 53 | 4-EtO | 5-Br | H | 1 | H | 253–256 (dec) | C | 0.088 ± 0.010[7] | | |
| 54 | 4-nPrO | 5-Br | H | 1 | H | 253–255 (dec) | C | 1.2 | | |
| 55 | 4-iPrO | 5-Br | H | 1 | H | 240–242 | C | 0.11 ± 0.02[7] | | |
| 56 | 4-nBuO | 5-Br | H | 1 | H | 256–258 | C | 1.1 | | |
| 57 | 4-NMe$_2$ | 5-Br | H | 1 | H | 285–287 (dec) | C | 0.033 ± 0.006[7] | | |
| 58 | 4-NMe$_2$ | 5-Cl | H | 1 | H | 283–286 (dec) | C | 0.087 | | |
| 59 | 4-NEt$_2$ | 5-Br | H | 1 | H | 247–249 | C | 0.047 | | |
| 60 | 4-MeS | 5-Br | H | 1 | H | 257–259 | C | 0.037 ± 0.010[7] | | |
| 61 | 4-CF$_3$ | H | H | 1 | H | 227–229 | A, D[3] | 0%, 53% (10 μM) | | |
| 62 | H | H | H | 2 | H | 202–204 | A, E | 20% (10 μM) | 11% (10 μM) | |

TABLE 1-continued

Melting Point, Preparative Method, and CCK and Gastrin Receptor Binding Data

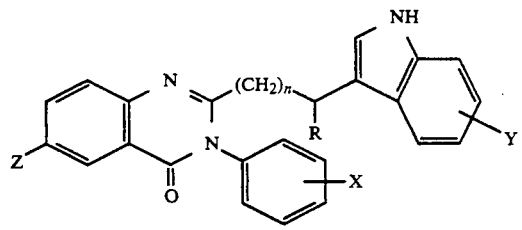

| Example | X | Y | Z | n | R | m.p. (°C.) | Procedure | Brain[1] | Pancreas[1] | Gastrin[1] |
|---|---|---|---|---|---|---|---|---|---|---|
| 63 | 3-MeO | 5-Br | H | 1 | Me | 208–211 | C | 0.10 | | |
| 64 | 3-Et | 5-Br | H | 1 | Me | 186–188 | C | 0.10 ± 0.01[7] | | 1.6 ± 0.1[7] |
| 65 | 3-MeO | H | H | 1 | ΦCH$_2$ | foam | C | 70% (10 μM) | | |
| 66 | 3-iPrO | 5-Br | Cl | 1 | H | 180–185 | C | 90% (1 μM) | | |

1. IC$_{50}$ (μM, Mean ± SEM) or % inhibition at specified concentration in binding assay. Values without SEM were obtained for n = 1.
2. Standard procedure except used DME as solvent in final reaction.
3. Standard procedure except used DME/DMF (50:30) as solvent in final reaction.
4. Standard procedure except used DME/DMF (1:1) as solvent in final reaction.
5. Final closure to the quinazolinone ring required refluxing the amide intermediate with TsOH in toluene with azeotropic removal of water.
6. Standard procedure except used collidine as solvent in final reaction.
7. n = 3

We claim:

1. A compound of the formula

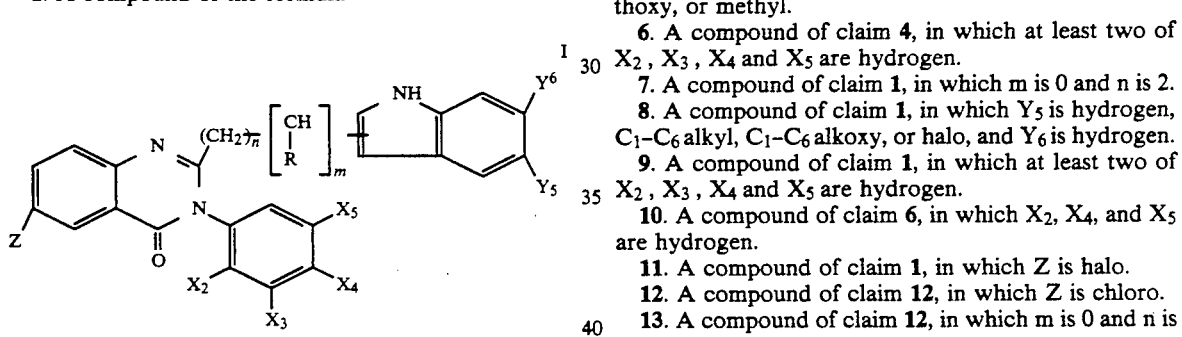

in which n is 1 or 2 and m is 0 or 1;
R is hydrogen, $C_1$–$C_4$ alkyl, benzyl, or phenyl;
Z is hydrogen or halo;
$X_2$, $X_3$, $X_4$, and $X_5$ are independently selected from the group consisting of hydrogen, halo, trifluoromethyl, $C_1$–$C_6$ alkoxy, $C_1$–$C_6$ alkyl, $C_1$–$C_6$ alkylthio, and —$NR_2R_3$, in which $R_2$ and $R_3$ are independently hydrogen, $C_1$–$C_4$ alkyl, benzyl, or phenyl, or $R_2$ and $R_3$ taken together with the nitrogen atom to which they are bonded form a 5- or 6-membered ring; or
$X_r$ and $X_{r+1}$, in which r is 2, 3, or 4, taken together form a divalent $C_3$–$C_5$ alkylene group or methylenedioxy; provided at least one of $X_2$, $X_3$, $X_4$, and $X_5$ is $NR_2R_3$ in which $R_2$ and $R_3$ taken together with the nitrogen atom to which they are bonded form a 6-membered ring; and
$Y_5$ and $Y_6$ are independently selected from the group consisting of hydrogen, $C_1$–$C_6$ alkyl, $C_1$–$C_6$ alkoxy, halo, and trifluoromethyl; and pharmaceutically acceptable salts thereof.

2. A compound of claim 1, in which Z is hydrogen.
3. A compound of claim 2, in which m is 0 and n is 2.
4. A compound of claim 3, in which $Y_5$ is hydrogen, $C_1$–$C_6$ alkyl, $C_1$–$C_6$ alkoxy, or halo, and $Y_6$ is hydrogen.
5. A compound of claim 4, in which $Y_5$ is halo, methoxy, or methyl.
6. A compound of claim 4, in which at least two of $X_2$, $X_3$, $X_4$ and $X_5$ are hydrogen.
7. A compound of claim 1, in which m is 0 and n is 2.
8. A compound of claim 1, in which $Y_5$ is hydrogen, $C_1$–$C_6$ alkyl, $C_1$–$C_6$ alkoxy, or halo, and $Y_6$ is hydrogen.
9. A compound of claim 1, in which at least two of $X_2$, $X_3$, $X_4$ and $X_5$ are hydrogen.
10. A compound of claim 6, in which $X_2$, $X_4$, and $X_5$ are hydrogen.
11. A compound of claim 1, in which Z is halo.
12. A compound of claim 12, in which Z is chloro.
13. A compound of claim 12, in which m is 0 and n is 2.
14. A compound of claim 13, in which $Y_5$ is chloro or bromo.
15. A compound of claim 1, in which m is 1 and R is selected from the group consisting of methyl, benzyl, and phenyl.
16. A compound of claim 15, in which n is 1.
17. A compound of claim 16, in which $Y_5$ is hydrogen or bromo and $Y_6$ is hydrogen.
18. A compound of claim 6, in which $X_3$ is $C_1$–$C_6$ alkyl.
19. A compound of claim 6, in which $X_3$ is $C_1$–$C_6$ alkoxy.
20. A method for inhibiting interaction of cholecystokinin with its receptors in a mammal and thereby antagonizing the influence of endogenous cholecystokinin, which comprises administering to said mammal a compound of claim 1 in an amount effective to antagonize the influence of cholecystokinin in said mammal.
21. A pharmaceutical formulation comprising, as the active ingredient, an effective amount of a compound of claim 1, and a pharmaceutically acceptable carrier, excipient, or diluent therefor.

* * * * *

UNITED STATES PATENT AND TRADEMARK OFFICE
CERTIFICATE OF CORRECTION

PATENT NO. : 5,196,427
DATED : March 23, 1993
INVENTOR(S) : Melvin J. Yu et al.

It is certified that error appears in the above-indentified patent and that said Letters Patent is hereby corrected as shown below:

Column 20, Claim 12 - delete "claim 12", and insert therefor
-- claim 11 --.

Signed and Sealed this

Twenty-eighth Day of December, 1993

Attest:

BRUCE LEHMAN

Attesting Officer     Commissioner of Patents and Trademarks